United States Patent
Schertiger et al.

(10) Patent No.: US 9,931,486 B2
(45) Date of Patent: Apr. 3, 2018

(54) CATHETER ASSEMBLY

(71) Applicant: Coloplast A/S, Humlebaek (DK)

(72) Inventors: Lars Olav Schertiger, Fredensborg (DK); Lars Stendevad Windeballe, Virum (DK)

(73) Assignee: Coyloplast A/S, Humlebaek (DK)

( * ) Notice: Subject to any disclaimer, the term of this patent is extended or adjusted under 35 U.S.C. 154(b) by 398 days.

(21) Appl. No.: 14/773,515

(22) PCT Filed: Mar. 7, 2014

(86) PCT No.: PCT/DK2014/050050
§ 371 (c)(1),
(2) Date: Sep. 8, 2015

(87) PCT Pub. No.: WO2014/135168
PCT Pub. Date: Sep. 12, 2014

(65) Prior Publication Data
US 2016/0022959 A1 Jan. 28, 2016

(30) Foreign Application Priority Data
Mar. 8, 2013 (DK) .................. 2013 70133

(51) Int. Cl.
*A61M 25/08* (2006.01)
*A61M 25/01* (2006.01)
*A61M 25/00* (2006.01)

(52) U.S. Cl.
CPC ....... *A61M 25/0111* (2013.01); *A61M 25/002* (2013.01); *A61M 25/0045* (2013.01); *A61M 25/0113* (2013.01); *A61M 2025/0046* (2013.01); *A61M 2025/0175* (2013.01); *A61M 2210/1096* (2013.01)

(58) Field of Classification Search
CPC ...... A61M 2025/0175; A61M 25/0113; A61M 25/0119
USPC ........................................... 604/544
See application file for complete search history.

(56) References Cited

U.S. PATENT DOCUMENTS

| | | | |
|---|---|---|---|
| 3,583,391 A | 6/1971 | Cox et al. | |
| 4,043,345 A | 8/1977 | Kramann et al. | |
| 5,171,305 A * | 12/1992 | Schickling | A61M 25/0119 604/271 |
| 5,662,703 A * | 9/1997 | Yurek | A61F 2/95 606/194 |
| 5,779,670 A | 7/1998 | Bidwell et al. | |
| 6,039,721 A * | 3/2000 | Johnson | A61F 2/958 604/103 |
| 6,059,813 A * | 5/2000 | Vrba | A61F 2/01 606/198 |
| 6,533,783 B1 | 3/2003 | Toellner | |

(Continued)

FOREIGN PATENT DOCUMENTS

| | | | |
|---|---|---|---|
| DE | 202005009947 U1 | 9/2005 | |
| EP | 0951919 A2 | 10/1999 | |

(Continued)

*Primary Examiner* — Susan Su
(74) *Attorney, Agent, or Firm* — Coloplast Corp.; Nick Baumann

(57) ABSTRACT

The invention provides a catheter (1) which is movable between an un-expanded and an expanded configuration by use of an advancing mechanism (20). The advancing mechanism facilitates safe and non-contaminated use of the catheter.

10 Claims, 7 Drawing Sheets

(56) References Cited

U.S. PATENT DOCUMENTS

| | | | |
|---|---|---|---|
| 2001/0044595 A1 | 11/2001 | Reydel et al. | |
| 2002/0099396 A1* | 7/2002 | Slaker | A61B 17/22031 606/159 |
| 2003/0168068 A1* | 9/2003 | Poole | A61B 1/00082 128/850 |
| 2003/0212411 A1* | 11/2003 | Jansen | A61M 25/0113 606/108 |
| 2005/0027236 A1 | 2/2005 | Douk | |

FOREIGN PATENT DOCUMENTS

| | | |
|---|---|---|
| WO | 04054653 A1 | 7/2004 |
| WO | 2012079581 A1 | 6/2012 |
| WO | 12126474 A1 | 9/2012 |
| WO | 2013029621 A1 | 3/2013 |

\* cited by examiner

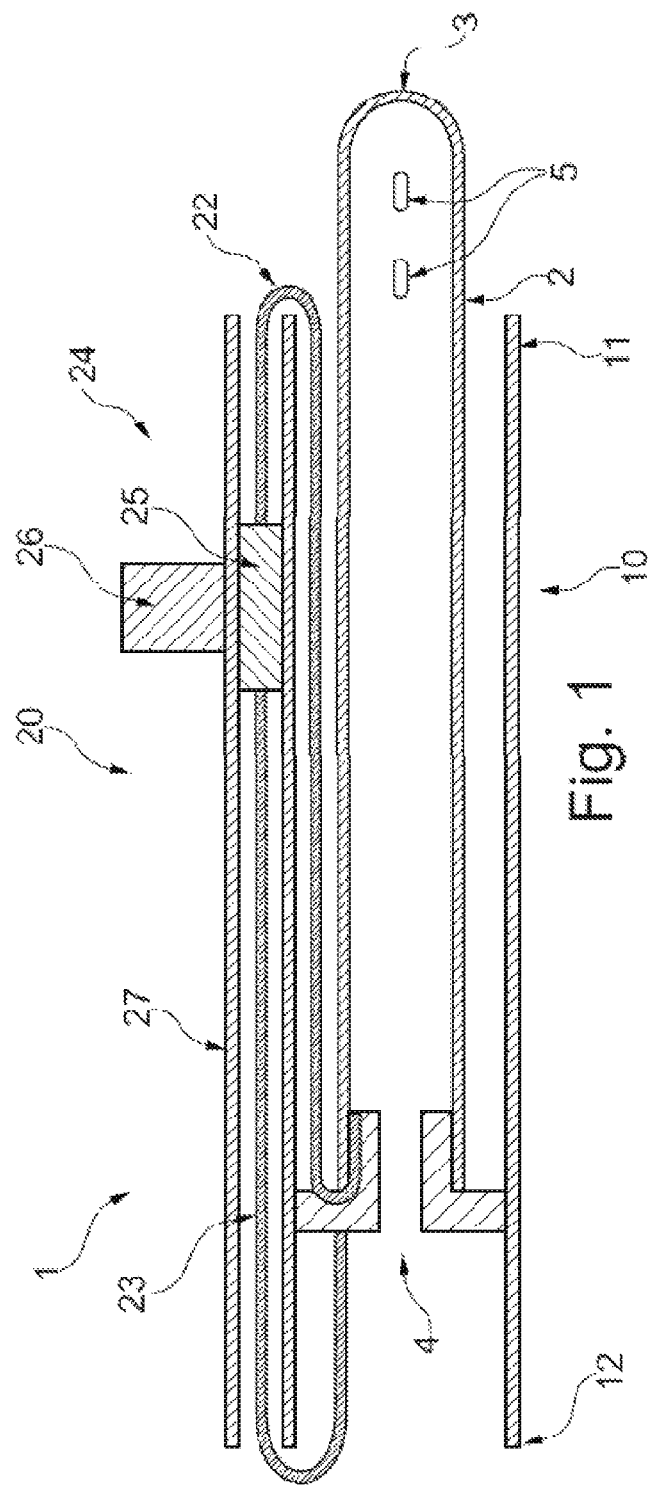
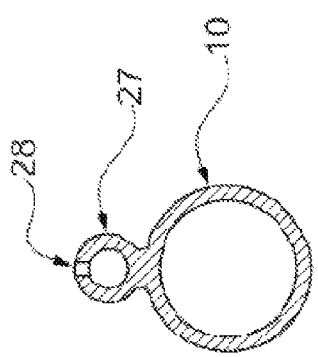
Fig. 1
Fig. 2

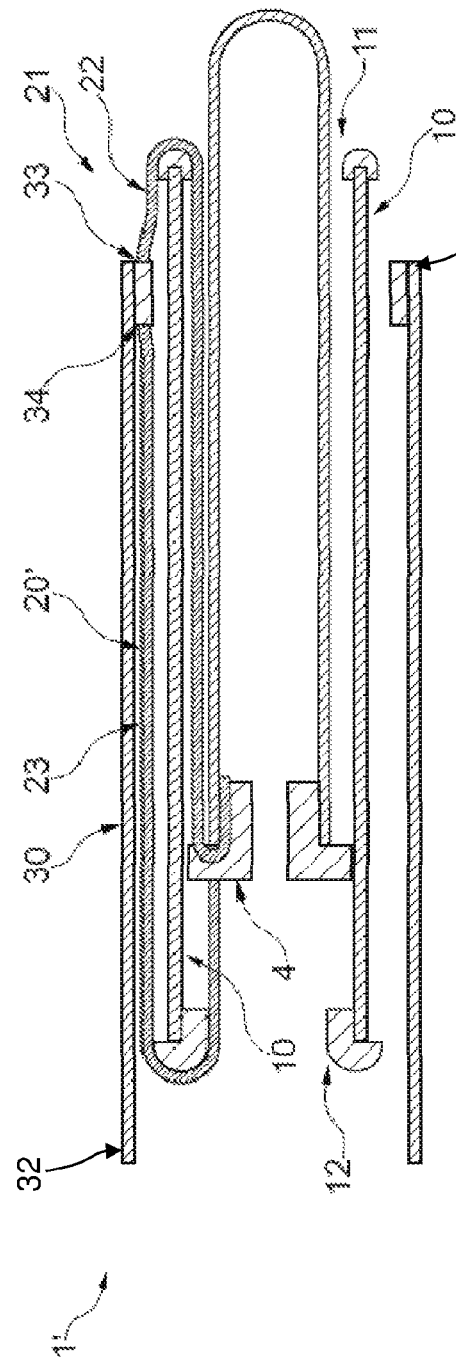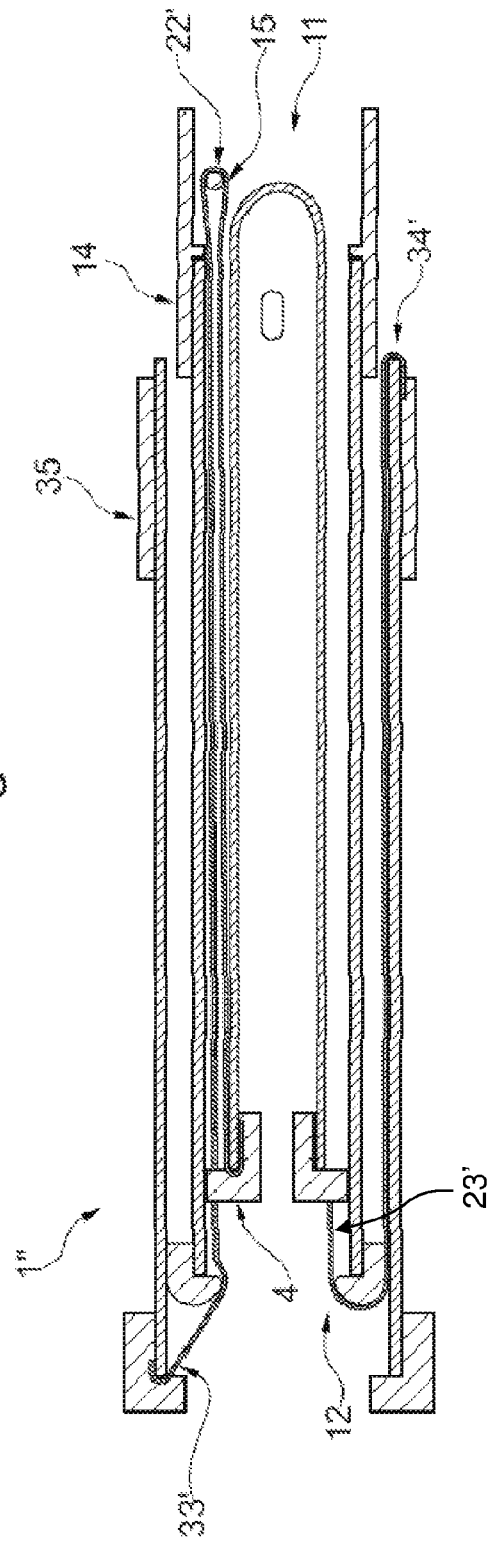

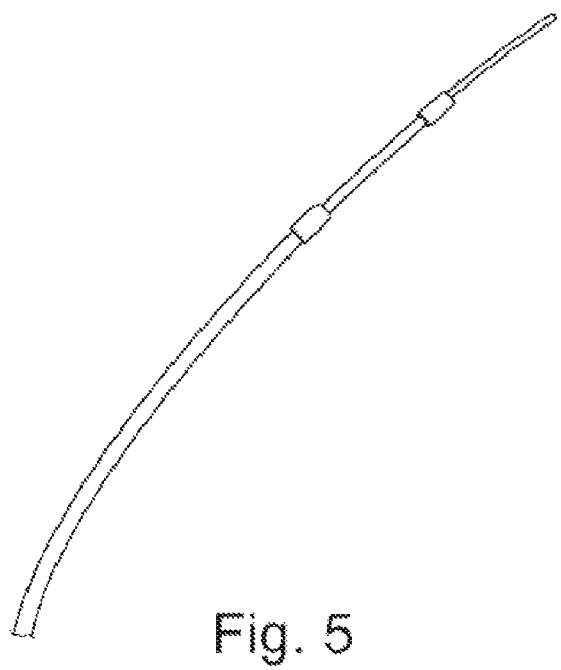
Fig. 5
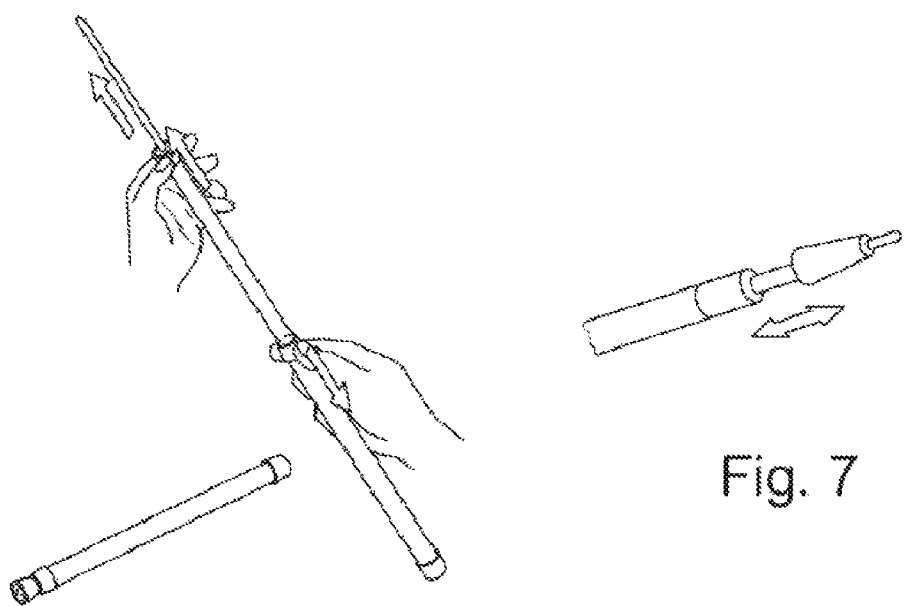
Fig. 7
Fig. 6

CATHETER ASSEMBLY

INTRODUCTION

The invention relates to a catheter assembly, particularly for intermittent catheterisation.

BACKGROUND

Urinary catheter assemblies for draining the bladder are increasingly used for intermittent as well as indwelling or permanent catheterisation. Typically, urinary catheters are used by patients suffering from urinary incontinence or by disabled individuals like paraplegics or tetraplegics, who may have no control permitting voluntary urination and for whom catheterisation may be the way of urinating.

Urinary catheters are divided into two major groups of catheters, indwelling catheters and intermittent catheters. Indwelling catheters are typically inserted into the urethra and the bladder by medical personal (i.e. a trained professional, typically a nurse or physician) and has means for retaining the catheter inside the bladder for up to two weeks or more.

Indwelling catheters are soft and flexible since they have to remain in the urethra for weeks. Indwelling catheters empty the bladder continuously.

Intermittent catheters are typically inserted by the user him- or herself and sits only in the urethra and bladder for as long as it take to empty the bladder—e.g. for about 5-10 minutes. Intermittent catheters are used every 4-6 hours to empty the bladder corresponding roughly to the interval that people having no urinary problems will usually go to the bathroom. Intermittent catheters are typically more rigid than indwelling catheters since they have to be inserted by the user him-/herself and since they do not need to sit in the urethra for days or weeks. An important feature for the intermittent catheter is to ease the insertion into the urethra. This is done by providing the intermittent catheter with a low friction surface. Non-limiting examples of such are hydrophilic coated catheters which are subsequently wetted by a swelling media in order to produce a low friction surface, or oil or water based gel which is applied to the catheter before insertion into the urethra.

Intermittent urinary catheters may be provided with a hydrophilic coating that needs to be wetted prior to use and thereby absorbs a considerable amount of liquid. Such a hydrophilic coating will provide a very lubricious surface that has very low friction when the catheter is to be inserted. Hydrophilic coated catheters, where the coating absorbs a considerable amount of liquid for a low friction surface (swelling degree >100%), will not be suitable for indwelling catheters, because the hydrophilic surface coating would stick to the mucosa inside the urethra if left inside the body for a longer period, due to the hydrophilic coating transforming from being highly lubricious when fully wetted to being adhesive when the hydration level of the coating is reduced.

This invention relates particularly to intermittent catheters.

DE202005009947U discloses a catheter that is sterilely wrapped in plastic and can be removed after a front segment of the packaging is broken off at the predetermined breaking line. A pulling string is attached to the distal end of the catheter and pushed through a guide element.

Generally, collapsible catheters including telescopic catheters are relatively short in their collapsed configuration and therefore easy to bring along, e.g. for use outside a comfort environment. Manipulation of such catheters into the ready to use, expanded, configuration may however, require training, it may compromise safety, particularly if insertable parts of the catheter is touched by hand during manipulation of the catheter, and it may be very difficult for the user having a reduced dexterity.

DESCRIPTION

It is an object of embodiments of this invention to provide an intermittent catheter which is easy to use even for people having reduced dexterity.

It is a further object to improve safety by reducing the risk of contamination of catheter parts which are inserted into the body.

It is a further object to improve the hygiene.

It is a further object to increase the wellbeing for the user of the intermittent catheter.

It is a further object to facilitate unpacking of a catheter.

It is a further object to facilitate simultaneous unpacking and insertion of a catheter.

These and other objects are meet by the invention which provides a catheter assembly comprising a catheter, a first tube, and a catheter advancing mechanism with an advancing element, the catheter and the first tube each extending in a distal direction from a proximal end to a distal end, and the catheter advancing mechanism being configured to move the catheter assembly telescopically between an unexpanded configuration where the catheter is arranged in a cavity within the first tube and an expanded configuration where at least an insertable part of the catheter is outside the cavity, the catheter advancing mechanism being configured to move the catheter assembly between the unexpanded and the expanded configuration by movement of the advancing element relative to the first tube.

Thus, the catheter assembly, by use of an advancing mechanism allows telescopic movement of the catheter assembly between the unexpanded and the expanded configuration and thereby provides for a non-touch preparation and insertion of the catheter into, and possibly also retraction of the catheter from, the bladder while the first tube protects the catheter. The catheter assembly can be used very easily, and due to the use of an advancing mechanism, the risk of bacterial infections in the urethra and bladder can be minimised as well as the contamination of the user's hands or clothes when the catheter is retracted. This means that the general level of hygiene and safety in connection with intermittent catheterisation is improved.

In the context of this application, whenever referring to a proximal end of an element of the invention, the referral is to the end adapted for insertion into the urethra/bladder, i.e. typically that end of the catheter provided with eyes for receiving urine from the bladder.

Whenever referring to the distal end of an element, the referral is to the end opposite the insertion end. In other words, the proximal end is the end closest to the user, when the catheter is to be inserted in the bladder of the user, and the distal end is the opposite end—the end furthest away from the user when the catheter is to be inserted. The same definitions apply to all elements of the invention. Accordingly, the proximal direction is the direction from the distal end to the proximal end and the distal direction is the opposite direction from the proximal end to the distal end. Likewise, longitudinal direction herein is the direction from the distal to the proximal end. The transverse direction is the direction transverse or even perpendicular to the longitudinal direction, which corresponds to the direction across the catheter.

The catheter described in this application may particularly be used as a urinary catheter, and particularly for intermittent urinary catheterisation by the user him or herself.

The catheter comprises a main tubular part extending from the distal end to the proximal end. The tip is positioned in the proximal end of the catheter and is provided as a rounded closed end of the tube constituting the main part of the catheter.

Usually catheters used as urinary draining devices are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm.

Catheters of this invention may prior to use be provided with a hydrophilic coating so as to impart a low-friction insertion. However other means to provide the required low-friction (for example gel or glycerol) may also be provided.

The hydrophilic coating may be provided only on the insertable part of the catheter. The insertable part of the catheter is the part adapted for insertion into the urethra/bladder.

The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick to the mucosa inside the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

The wetting medium for activating the hydrophilic catheter may be confined or partly confined in a sponge or in cloth or similar woven or non-woven material etc.

The wetting medium may be in liquid or gas phase.

The catheter package may comprise a medium for activating the hydrophilic surface coating of the catheter. The activating medium may be a water based substance, such as sterile water, saline-solution, or any water based liquid. Furthermore, the activating medium may be in the form of a vapour contributing material, such as a wetted sponge, woven or non-woven material comprising a vapour contributing liquid. By introducing a vapour contributing material into the package, the vapour will over time hydrate the hydrophilic coating ensuring that the coating is activated and that the hydrophilic coating provides a low-friction surface for the insertable part of the catheter.

In an embodiment of the invention, the first tube additionally functions as a storage container for the catheter. This means that the first tube is made of a material that is substantially impermeable to bacteria so that the catheter is maintained sterile through-out the storage time—typically up to 3 to 5 years. In a related embodiment, the first tube is substantially water-vapour impermeable so that a wetted or hydrated catheter and possible liquid swelling medium can be contained in the first tube for the storage time.

The assembly may further comprise a second tube arranged about the first tube and extending in the distal direction from a proximal end to a distal end.

The first and second tube may particularly be telescopically movable relative to each other, and the second tube may particularly constitute or at least form part of the advancing element such that the assembly is moved between the non-expanded and the expanded state by movement of the first tube relative to the second tube. In this embodiment, the first tube forms an intermediate tube about the catheter and the second tube forms an outer tube about the first tube. In this embodiment, the second tube may either alone, or in combination with the first tube, function as a storage container for the catheter. This means that the second tube could be made of a material that is substantially impermeable to bacteria so that the catheter is maintained sterile through-out the storage time—again, typically up to 3 to 5 years. The second tube could be substantially water-vapour impermeable so that a wetted or hydrated catheter and possible liquid swelling medium can be contained in the extension tube for the storage time.

As an example, the material for the first and/or the second tube may be as described in international publication no's WO2012/016570 or WO2012/016571.

Further, since the first and second tubes are arranged about the catheter, the radial size increases, and the increased radial size facilitates a better grip, particularly for the disabled or partly disabled user having reduced dexterity.

In another embodiment, the catheter assembly is further wrapped in a foil-material providing the desired bacteria barrier or water vapour barrier. Such foil-materials are well-known in the art.

In a first series of embodiments, the catheter assembly according to the invention comprises an advancing mechanism with a string means and in a second series of embodiments the catheter assembly according to the invention comprises an advancing mechanism with a fluid. In further embodiments, the first and second embodiments are combined such that the advancing mechanism comprises strings in combination with fluid.

The string means could be attached to the catheter or rather attached between the catheter and the advancing element such that the advancing element can be used for moving the catheter relative to the first tube by use of the string means.

The string means comprises a first string element extending between the catheter and a first attachment point and being adapted to provide a pulling force in the proximal direction and it is therefore capable of moving the catheter relative to the first tube in the proximal direction and at least partly out of the cavity thereby exiting the catheter from the first tube. The first attachment point is therefore typically a fixed point on the advancing element.

The first string element could be threaded and thereby extend along the catheter, particularly from the distal end of the catheter. The first string may extend in the proximal direction, out through the proximal end of the first tube and back in the distal direction along an outer surface of the first tube to the first attachment point. In this embodiment, the first string element thereby extends in both the proximal and in the distal direction on opposite sides of the wall of the first tube.

Alternatively, the first string element may extend along the catheter in the proximal direction, around a turning point and back in the distal direction along an inner surface of the first tube. In this way, the first string element extends in both the proximal and in the distal directions inside the first tube.

To enable collapsing of the catheter back into the non-expanded configuration, the string means may further comprise a second string element extending between the catheter and a second attachment point and being adapted to provide a pulling force in the distal direction for moving the catheter relative to the first tube in the distal direction thereby re-entering the catheter into the first tube.

The second string element may be threaded to extend from the catheter, particularly from the distal end of the catheter, and in the distal direction, out through the distal end of the first tube and back in the proximal direction along an outer surface of the first tube.

In other words, the first string element may extend from the distal end of the catheter, along the catheter and around the proximal end of the extension tube to a first attachment point. Likewise, the second string element may extend from the distal end of the catheter, around the distal end of the extension tube to a second attachment point. Thus in the context of this application threaded means that the string extends in that direction.

The first and second attachment points may be directly adjacent or even overlying each other, or the first and second strings may even be connected or form one single string so that the string means forms a closed loop from the catheter to the attachment points and back to the catheter.

When the advancing element is constituted by a second tube, the second string element may extend in the proximal direction along an outer surface of the first tube inside the second tube. In that way, the second string element is shielded from the user by the second tube.

In a related embodiment, the first and second attachment points are attached to a gripping mechanism in such a way that the first and second string elements provide the pulling force as a result of movement of the gripping mechanism relative to the first tube. The advancing element may therefore form part of the gripping element.

The gripping mechanism provides a larger surface for gripping than the catheter in itself offers. This makes the catheter set easier to handle for users with poor hand dexterity.

The gripping mechanism may in one embodiment comprise a first element located to move along an outer surface of the first tube.

In one particular embodiment, the gripping mechanism is combined with advancing element in the form of a second tube. In this embodiment, the gripping mechanism may comprise a first element being movable in a space between the first and the second tube. The first element may be movable by use of a handle moving along an outer surface of the second tube. The handle and the first element may be connected magnetically, i.e. such that the movement of the handle is transferred to the first element by magnetic attraction forces. Alternatively, the handle and the first element are connected physically via a slit or other form of opening in the second tube.

In an embodiment of the invention, the string means are substantially non-extensible. By substantially non-extensible is meant a string that will not extend during the normal use of the string means in the catheter advancing mechanism. In other words the substantially non-extensible means that the extension of the string during normal use is less than 5%. As an example it may be made of a fishing line such as "FireLine Fused Crystal" marketed by Berkley. Substantially non-extensible string means have the advantage that there is an immediate or direct coupling between the movement done by the user and the movement of the catheter into and out of the extension tube.

In a particular embodiment, the assembly comprises a catheter and a first extension tube telescopically connected to each other, the assembly further comprising a catheter advancing mechanism including string means attached to the distal end of the catheter, the string means comprising a first string element adapted for providing a pulling force in the proximal direction for exiting the catheter form the first extension tube and a second string element adapted for providing a pulling force in the distal direction for re-entering the catheter into the first extension tube.

In another particular embodiment, the attachment points are positioned at the inside of the second extension tube. This means that the first string element is threaded from the distal end of the catheter, along the catheter in the proximal direction, exits the first extension tube at the proximal end, the first string element is further threaded along the outside of the first extension tube in the distal direction and into the second extension tube to a first attachment point on the inside of the second extension tube. The second string element is in this embodiment threaded from the distal end of the catheter in the distal direction, exits the first extension tube at the distal end, the second string element is further threaded along the outside of the first extension tube in the proximal direction inside the second extension tube to a second attachment point on the inside of the second extension tube. When a catheter assembly according to this embodiment is to be used, the user grips the second extension and the first extension tube and moves the first extension tube in the proximal direction with respect to the second extension tube. This is an intuitive motion because the catheter has to exit proximally. Due to the threading of the string elements, this will lead to the catheter exiting the first extension tube. Thus the user can insert the catheter without touching it. When the urine has been drained from the catheter, the user moves the first extension tube in the distal direction with respect to the second extension tube. Due to the threading of the string elements, this will lead to the catheter being re-entered into the first extension tube. Thus the user can hygienically remove the catheter from the urethra again. Furthermore, during insertion, the user may have to retract the catheter slightly and try to insert it again, if for example it is difficult to move insert the catheter past the prostate. This retraction and insertion procedure can easily be done without touching the catheter.

In another embodiment, the first attachment point is positioned in the distal end of the second extension tube and the second attachment point is positioned in the proximal end of the second extension tube. In this embodiment, the first string element is threaded from the distal end of the catheter, along the catheter in the proximal direction, exits the first extension tube at the proximal end, the first string element is further threaded along the outside of the first extension tube in the distal direction and into the second extension tube to a first attachment point positioned on the inside at the distal end of the second extension tube. The first string element may also be threaded from the distal end of the catheter, along the catheter in the proximal direction, around a turning point positioned close to the proximal end of the first extension tube, back along the catheter inside the first extension tube in the distal direction, exits the first extension tube in the distal end and is attached to a first attachment point positioned at the distal end of the second extension tube. The second string element is in this embodiment threaded from the distal end of the catheter in the distal direction, exits the first extension tube at the distal end, the second string element is further threaded along the outside of the first extension tube in the proximal direction inside the second extension tube to a second attachment point on the proximal end of the second extension tube.

In the second series of embodiments, the catheter is telescopic and comprises a proximal catheter section with a proximal conduit section having an inlet for receiving urine from a body cavity and a distal catheter section with a distal conduit section forming an outlet for draining urine from the telescopic urinary catheter and being in liquid flow communication with the proximal conduit section, the distal catheter section being telescopically movable relative to the proximal catheter section to thereby move the catheter assembly telescopically between the unexpanded and expanded configuration, wherein the catheter assembly further comprises a discharge chamber configured to discharge a fluid by movement of the first tube and the advancing element relative to each other, a pressure chamber arranged to receive fluid discharged from the discharge chamber, and a catheter piston attached to one of the proximal and distal catheter sections and being movable in response to a fluid pressure in the pressure chamber to thereby move the proximal catheter section relative to the distal catheter section and thereby move the catheter assembly from the unexpanded to the expanded configuration when the fluid is received from the discharge chamber.

The discharge chamber could be formed between the first tube and the advancing element, the first tube and the advancing element being movable relative to each other such that a volume of the chamber can be reduced to thereby discharge the fluid into the pressure chamber. This provides an embodiment where the user can move the first tube and the advancing element relative to each other and thereby move the telescopic catheter to the expanded configuration in an easy way. The displaceable volume may e.g. be in the range of 2-4 ml. such as 3.5 ml. for catheter assemblies for female users and in the range of 8-12 ml. such as 10 ml for male users.

Again, the first tube may form an intermediate tube at least partly enclosing the catheter, and the advancing element may form a second tube, particularly an outer tube which at least partly encloses the intermediate tube. In this way, the first tube and the second tube may protect the catheter and a compact assembly can be obtained where the catheter is packed inside the tubes in line with the packaging of the catheter in the first and/or second tube as described already herein.

The catheter assembly may comprise a number of seals providing sealing during sliding of the elements relative to each other. Particularly, the assembly may comprise a first seal fixed to the proximal catheter section and arranged to slide along an inner surface of the first tube; a second seal fixed to the first tube and arranged to slide along an inner surface of the advancing element or second tube; and a third seal fixed to the advancing element or second tube and arranged to slide along an outer surface of the first tube.

Particularly, the first tube and the advancing element may be telescopically connected such that they can be moved relative to each other in the longitudinal direction. This is particularly relevant when the advancing element is in the form of the mentioned second tube.

The first tube and the advancing element may further be telescopically connected to the telescopic urinary catheter such that they can be moved relative to the telescopic catheter in the longitudinal direction.

The catheter package may further comprise a wetting receptacle housing at least an insertable part of the catheter, e.g. accommodating the proximal catheter section. The wetting receptacle may be arranged to receive fluid discharged from the discharge chamber and thereby facilitate wetting of an insertable part of the catheter. For this purpose, the fluid may particularly be a wetting medium for wetting of the catheter or at least an insertable part of the catheter. Such wetting may e.g. be for the purpose of sterilising the catheter, for obtaining a low friction surface, or for adding a drug substance to the surface of the catheter.

In one embodiment, the fluid is suitable for swelling a hydrophilic surface of the catheter. The fluid may e.g. be a water based substance, such as sterile water, saline-solution, or any water based liquid.

The wetting receptacle may be in fluid communication with the discharge chamber via a first communication opening configured to discharge the fluid from the discharge chamber into the wetting chamber at a pressure $\rho$.

The pressure chamber may be in fluid communication with the discharge chamber via a second communication opening configured to discharge the fluid from the discharge chamber into the pressure chamber at a pressure $\rho_1$ which is higher than $\rho$.

Each of the first and second communication opening may be made as one or several small holes, e.g. where the size and/or shape of the hole or holes provide the desired pressure needed to discharge the fluid. In some embodiments the hole or holes may be covered by a weak material, e.g. thin aluminium or plastic. For example a 0.02 mm aluminum foil, that may be laser cut so as to provide the right opening pressure. Again, different pressures may be provided by use of different covering material or use of material in different layer thickness.

Due to the different pressures $\rho$ and $\rho_1$, the fluid may be prevented from entering the pressure chamber until the fluid has entered the wetting receptacle, and the user may be ensured that the catheter is wetted before it moves from the unexpanded to the expanded configuration and use of an un-wetted catheter can therefore be prevented.

The third seal could be movable across the first communication opening by movement of the first tube relative to the advancing element. Particularly, the third seal may thereby close the first communication opening such that the fluid can no longer enter the wetting receptacle when the seal has closed the opening.

In this embodiment, the user can move the first tube and the advancing element relative to each other in a first preparation sequence. In this sequence, the fluid is discharged into the wetting receptacle. When the third seal reaches the first communication opening and closes the opening, continued movement of the first tube relative to the advancing element forces the fluid into the pressure chamber and thereby moves the catheter towards the expanded configuration.

One of the proximal and distal catheter sections, preferably the distal catheter section, may be fixed to, or it may form part of the first tube, and the other one of the proximal and distal catheter sections is movable relative to the first tube.

In line with the first series of embodiments, the telescopic urinary catheter may comprise a hydrophilic surface, and the fluid is a swelling fluid capable of activating the hydrophilic surface to reduce the friction of the hydrophilic surface.

In one embodiment, the catheter assembly is further wrapped in a foil-material providing the desired bacteria barrier or water vapour barrier. Such foil-materials are well-known in the art.

Furthermore, the first tube may form an extension tube which provides an extension for leading the urine into a toilet so that the user may be seated in a wheel-chair and use the assembly, without having to move to the toilet. The user simply inserts the catheter into the urethra and use the extension tube to lead the urine into the toilet.

In a similar manner the mentioned second tube may form a further extension tube which provides a larger extension for leading the urine into a toilet.

Any of the features mentioned relative to the first series of embodiments may be combined with the features mentioned relative to the second series of embodiments.

In a second aspect, the invention provides a method of operating a catheter of the kind described herein. The method comprises the step of moving the first tube and the advancing element relative to each other to thereby move the catheter assembly between the unexpanded and the expanded configuration.

LIST OF DRAWINGS

Embodiments of the invention will now be described in further details with reference to the drawings, in which:

FIG. 1 illustrates a first embodiment of the invention in cross-section seen from the side;

FIG. 2 illustrates the first embodiment in cross-section seen from the end;

FIGS. 3 and 4 illustrate cross-sectional side views of different embodiments of the invention including a first and a second tube;

FIG. 5 illustrates an embodiment of the invention;

FIG. 6 illustrates how the user can use a catheter assembly of the invention;

FIG. 7 illustrates the gripping means of an embodiment of the invention;

DESCRIPTION OF EMBODIMENTS

Figure 8:
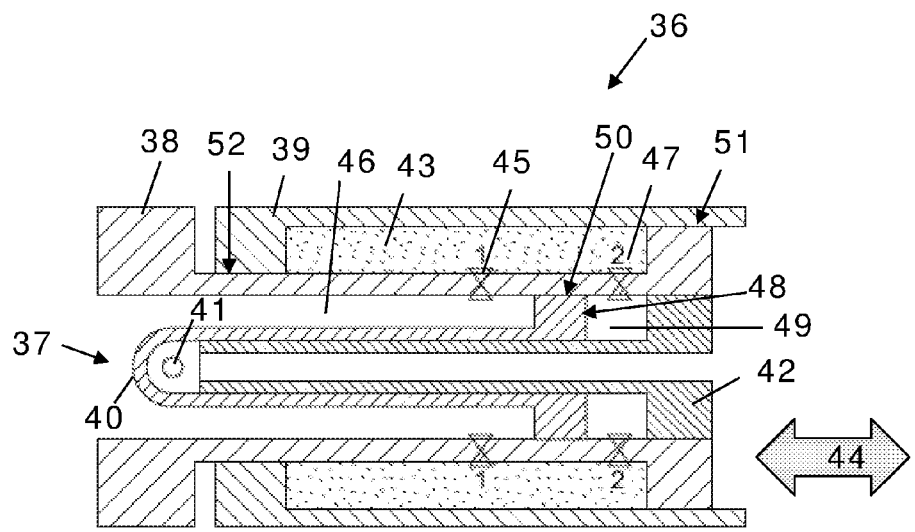
FIGS. 8-10 illustrate a catheter assembly according to the second series of embodiments of the invention.

It should be understood that the detailed description and specific examples, while indicating embodiments of the invention, are given by way of illustration only, since various changes and modifications within the spirit and scope of the invention will become apparent to those skilled in the art from this detailed description.

FIG. 1 illustrates a cross-sectional view of a catheter assembly 1 according to a first series of embodiments the invention. The catheter assembly 1 comprises a catheter 2 with a proximal insertion end 3 and a distal end 4. The distal end 4 is wider than the tubular part of the catheter. The catheter is further provided with eyelets 5 for leading urine from the bladder into the inner lumen of the catheter. In the figure, the catheter 2 is contained in a first tube 10, see e.g. FIG. 5 showing the embodiment in a perspective view. The widened distal end 4 provides a slight friction against the inner surface of the first tube 10 so as to prevent the catheter from accidentally falling out. The first tube 10 has a proximal end 11 and a distal end 12 and can be used as an extension of the catheter for draining urine into a place of disposal.

The assembly further includes a catheter advancing mechanism 20 comprising close-looped string means 21 coupled to the distal end 4 of the catheter. The string means 21 has a first element 22 and a second element 23. The first string element 22 is threaded from the distal end 4 of the catheter and along the catheter in the proximal direction until it exits the first tube 10 at the proximal end 11. From there the first string element is threaded in the distal direction along the outside of the first tube 10 to a first attachment point (not shown) at a gripping mechanism 24. The second string element 23 is threaded from the distal end 4 of the catheter in the distal direction until it exits the first tube 10 at the distal end 12. From there the second string element 23 is threaded in the proximal direction along the outside of the first tube 10 to a second attachment point (not shown) at a gripping mechanism 24. In the illustrated embodiment, the gripping mechanism comprises a runner 25 and a gripping plate 26 attached to the runner 25. The runner 25 comprises the attachment points—in other words the string elements 22 and 23 are attached to the runner 25. The runner 25 is in this embodiment positioned in groove 27 provided on the outside of the first tube 10—see FIG. 2. The groove 27 has a slit towards the top 28 so that the gripping plate 26 can pass along the groove 27. Prior to use, the first tube 10 may be closed by closures (not shown) in each end.

FIG. 3 illustrates another catheter assembly 1' according to the invention. The same reference numbers are used for the same elements. In this embodiment, a second tube 30 is telescopically connected to the first tube 10. The second tube 30 has a proximal end 31 and a distal end 32 and forms a further extension of the catheter for leading urine to the place of disposal.

In this embodiment, the assembly comprises a catheter advancing mechanism 20' comprising close-looped string means coupled to the distal end 4 of the catheter. The string means has a first element 22 and a second element 23. In this embodiment the first string element 22 is threaded from the distal end 4 of the catheter and along the catheter in the proximal direction until it exits the first tube 10 at the proximal end 11. From there the first string element 22 is threaded in the distal direction along the outside of the first tube 10 to a first attachment point 33 at the inside of the second tube 30. The second string element 23 is threaded from the distal end 4 of the catheter in the distal direction until it exits the first tube 10 at the distal end 12. From there the second string element 23 is threaded in the proximal direction along the outside of the first tube 10 to a second attachment point 34 at the inside of the second tube 30.

FIGS. 4 to 7 illustrate a further embodiment of a catheter assembly 1" according to the invention. FIG. 4 illustrates a cross-sectional view of the catheter assembly 1", FIG. 5 illustrates the catheter assembly 1", FIG. 6 illustrates how a catheter assembly 1" can be used and FIG. 7 illustrates a detail relating to gripping indicators. The same reference numbers are used to indicate the same elements as in FIGS. 1 to 3. Also in this embodiment, a second tube 30 is used. In this embodiment, the first string element 22' is threaded from the distal end 4 of the catheter, proximally along the catheter and around a turning point 15 positioned inside the first tube 10 close to the proximal end 11. From there, the first string element 22' is threaded distally towards and past the distal end of the catheter to exit the first tube 10 at the distal end 12. The first string element 22' is attached to the second tube 30 at a second attachment point 33' the distal end 32. The second string element 23' is threaded from the distal end 4 of the catheter, distally out of the first tube at the distal end 12 and from there proximally along the first tube 10 inside the second tube 30 to be attached at a second attachment point 34' at the proximal end 31. In the embodiment illustrated, the first tube 10 and the second tube 30 are both provided with gripping indicators 14, 35 at the proximal end.

When the catheter assembly 1″ is to be used (see FIGS. 6 and 7), the user grips the gripping indicators 14, 35 at the first and second extension tube and pulls the first tube 10 in the proximal direction as indicated in the figure. Thereby the catheter exits from the proximal end. To retract the catheter, the user pushes the extension tube 10 in the distal direction with respect to the second tube 30 (see FIG. 7) and the catheter will be retracted into the first tube 10.

Figure 9:
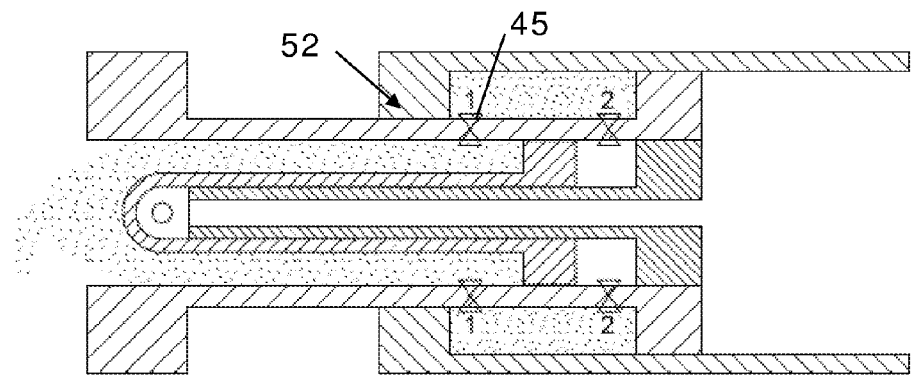
Figure 10:
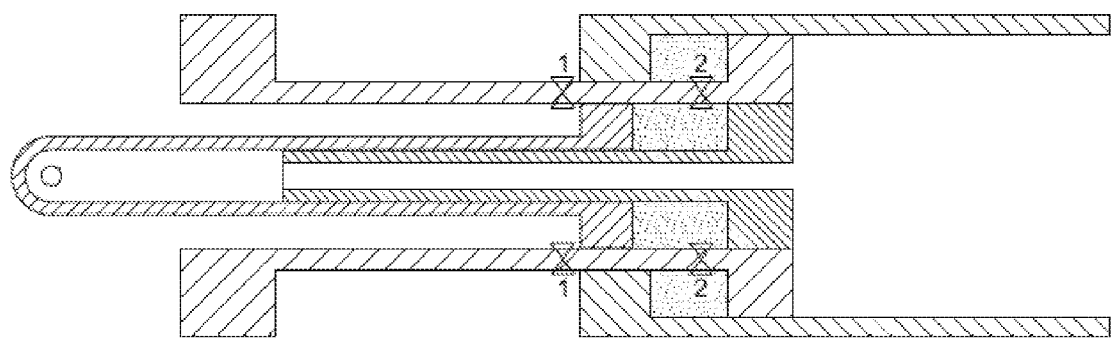

FIGS. 8-10 illustrate cross-sectional views of a second series of embodiments. The drawings are not to scale. The dimensions of the walls etc. in the cross-section are exaggerated for clarifying the relationship between them. In this embodiment, the catheter assembly 36 comprises a telescopic urinary catheter 37, a first, intermediate, tube 38 which encloses the catheter, and an advancing element in the form of a second, outer, tube 39 which encloses the intermediate tube. The assembly further comprises closure elements (not shown) e.g. in the form of caps or closure tabs, to close off the assembly during storage.

The telescopic urinary catheter 37 comprises a proximal catheter section 40 with a proximal conduit section extending from a distal end to a proximal end. At the proximal end, the proximal section comprises an inlet 41 for receiving urine from the bladder of the user. The inlet is smoothly rounded to prevent damages of the mucosa.

The distal catheter section 42 forms inside a distal conduit section. In a proximal end of the distal conduit section, the distal conduit section is in fluid communication with the proximal conduit section. In its opposite distal end, the distal conduit section forms an outlet for draining urine from the telescopic urinary catheter into the toilet or into a collection bag etc.

An outer surface of the distal catheter section is arranged to slide along an inner surface of the proximal catheter section whereby the catheter becomes telescopically movable between an unexpanded, short, configuration and an expanded, long, configuration.

The intermediate tube and outer tube defines a discharge chamber 43 with a volume which can be changed by movement of the tubes relative to each other as indicated by the arrow 44.

The discharge chamber contains a fluid which can be discharged through the first communication opening 45 into a wetting receptacle 46, or through the second communication opening 47 into a pressure chamber 49.

The first and second communication openings opens at different fluid pressures such that the first communication opening opens at a pressure ρ, and the second communication opening opens at a pressure ρ1 which is higher than ρ.

Due to the pressure difference between ρ1 and ρ, the first communication opening will open firstly, and therefore allow the fluid to be drained from the discharge chamber 43 into the wetting receptacle 46 which houses the proximal end of the catheter which is configured for insertion into urethra.

The fluid is thereby, in a first step, used for treating the insertable part of the catheter. The treatment could relate to:
  swelling of a hydrophilic surface of the insertable part of the catheter for making the catheter more slippery and thereby ease the insertion. For this purpose, the fluid could be water, or a saline solution, e.g. containing a mixture of water and PVP;
  sterilization of the catheter. For this purpose, the fluid could be, or it may include, a fungicide or a sterilizing agent;
  preparation of the catheter with a medical active component, e.g. lidocaine for main relief, or with an antibiotic compound e.g. for preventing or treating infections;
  traditional lubrication. For this purpose, the fluid could be a gel, e.g. a water based gel, wax, oil or other kinds of lubricating substance.

The telescopic catheter, and particularly the distal section thereof, may form a catheter piston 48 which is arranged to form a wall in the pressure chamber 49 such that it is influenced by a fluid pressure in the pressure chamber. When the fluid is discharged through the second communication opening 47 into the pressure chamber 49, the telescopic urinary catheter is thereby moved between the unexpanded and the expanded configuration. The catheter piston is arranged also to slide along an inner surface of the intermediate tube.

To seal the pressure chamber and prevent leakage therefrom, the catheter assembly has a first seal 50 fixed to the proximal catheter section and arranged to slide along the inner surface of the intermediate tube.

To seal the discharge chamber and prevent leakage therefrom, the catheter assembly has a second seal 51 and a third seal 52. The second seal is fixed to the intermediate tube and arranged to slide along an inner surface of the outer tube, and the third seal is fixed to the outer tube and arranged to slide along an outer surface of the intermediate tube.

In FIG. 8, the catheter assembly is in an initial state, i.e. illustrated before movement of the first element relative to the second element. In this state, the fluid is entirely contained in the discharge chamber and the telescopic catheter is in its collapsed state.

FIG. 9 illustrates the assembly in a state where a part of the fluid has been displaced into the wetting receptacle, but due to the different opening pressures at the first and second communication openings, nothing has been displaced into the pressure chamber yet. The assembly is close to a position where the first communication opening 45 becomes sealed by the third seal 47. The third seal thereby prevents displacement of fluid through the first communication opening. By further movement of the first and second elements relative to each other, the fluid is therefore necessarily discharged through the second communication opening whereby the telescopic catheter moves towards the expanded state.

FIG. 10 illustrates a state where the first and second elements are moved relative to each other until they reach an end position where nearly all the fluid is displaced into the wetting receptacle and into the pressure chamber. The telescopic catheter is now moving towards the expanded state.

Figure 11:
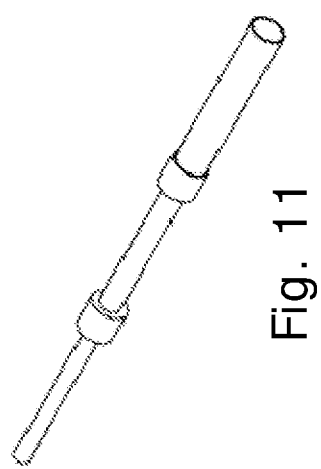
FIGS. 11, 12 and 13 illustrate different views of the assembly.
Figure 12:
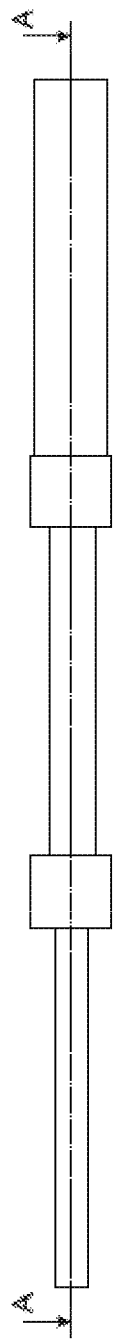
Figure 13:
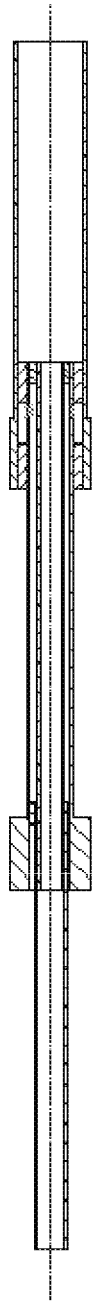

FIGS. 11, 12 and 13 illustrate different views of the assembly in a fully expanded and ready to use state. FIG. 13 is a cross section at AA in FIG. 12.

Figure 14:
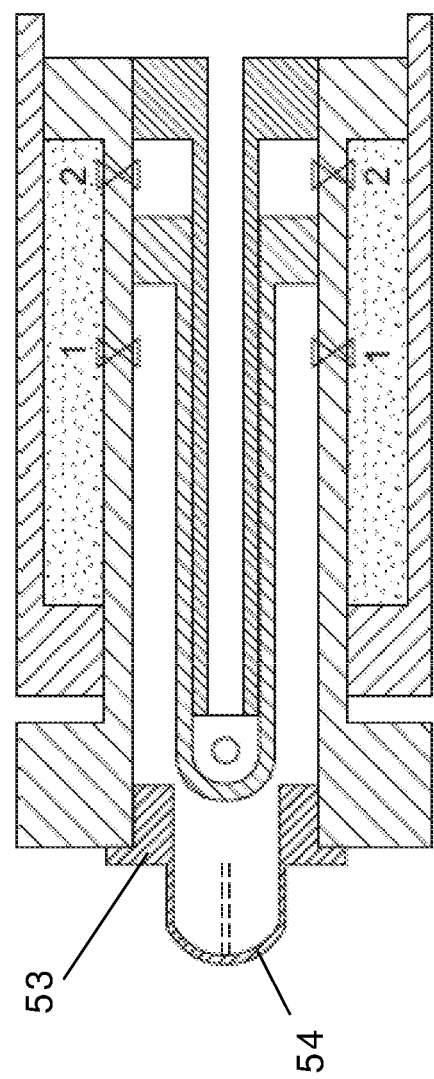
FIG. 14 illustrates an insertion aid 53 attached to the proximal end of the first tube.

FIG. 14 illustrates an insertion aid 53 attached to the proximal end of the first tube. The insertion aid 53 has a smoothly rounded tip 54 which can be received in the opening of urethra, and the proximal catheter tip can subsequently be pushed through the insertion aid and further into the urethra. The insertion aid may prevent transfer of bacteria and other contaminants from the opening of the urethra and further into the urethra.

Figures 15A, 15B, 15C:
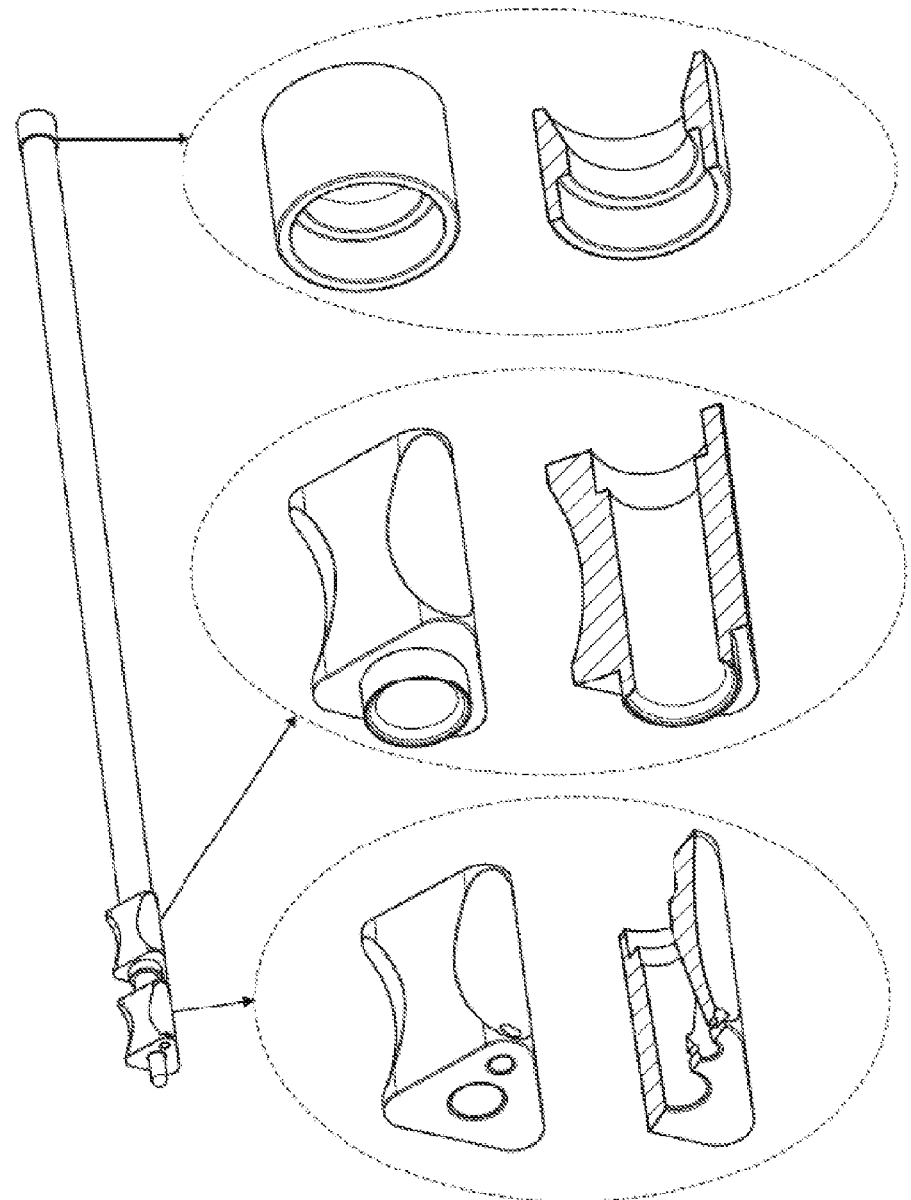
FIGS. 15a, 15b, and 15c illustrate different grips.

FIGS. 15a, 15b, and 15c illustrate three different shapes of grips attachable to one or both of the first tube and the advancing element (or second tube). The grips facilitate a better grip for the person having reduced dexterity.

The insertion aid illustrated in FIG. 14 and the grips in FIG. 15 can be used both in combination with the first and the second series of embodiments according to the disclosed invention.

The invention claimed is:

1. A catheter assembly comprising:
   a catheter,
   a first tube, and
   a catheter advancing element, each of the catheter and the first tube extending between a proximal end and a distal end,
   wherein the catheter advancing element is configured to shift the catheter assembly telescopically between an unexpanded configuration in which the catheter is arranged in a cavity within the first tube, and an expanded configuration in which an insertable part of the catheter is located outside the cavity by moving the catheter advancing element relative to the first tube, and
   wherein the catheter advancing element comprises a first string element extending between the catheter and a first attachment point and a second string element extending between the catheter and a second attachment point.

2. A catheter assembly according to claim 1, wherein the first string element extends along the catheter in a proximal direction, out through the proximal end of the first tube and further in a distal direction along an outer surface of the first tube.

3. A catheter assembly according to claim 1, wherein the first string element extends along the catheter in a proximal direction, around a turning point and continues in a distal direction along an inner surface of the first tube.

4. A catheter assembly according to claim 1, wherein the first attachment point is located on the catheter advancing element.

5. A catheter assembly according to claim 1, wherein the second string element extends from the catheter in a distal direction, out through the distal end of the first tube and further in a proximal direction along an outer surface of the first tube.

6. A catheter assembly according to claim 1, further comprising a second tube arranged about the first tube and extending in a distal direction from a proximal end of the second tube to a distal end of the second tube.

7. A catheter assembly according to claim 6, wherein the second tube forms a portion of the catheter advancing element.

8. A catheter assembly according to claim 5 and claim 7, where the second string element extends further in the proximal direction along an outer surface of the first tube inside the second tube.

9. A catheter assembly according to claim 1, further comprising a gripping mechanism forming a portion of the catheter advancing element, wherein one of the first and second string elements is fixed to the gripping mechanism to provide a pulling force in response to movement of the gripping mechanism.

10. A catheter assembly according to claim 9, wherein the gripping mechanism is movable relative to the first tube.

* * * * *